United States Patent
Johnson et al.

(10) Patent No.: US 8,122,892 B2
(45) Date of Patent: Feb. 28, 2012

(54) WATER ABSORBING EAR PLUGS

(75) Inventors: Chris Johnson, Laguna Beach, CA (US); Drew O'Connell, Cold Spring Harbor, NY (US)

(73) Assignee: Cirrus Healthcare Products, LLC, Cold Spring Harbor, NY (US)

( * ) Notice: Subject to any disclaimer, the term of this patent is extended or adjusted under 35 U.S.C. 154(b) by 216 days.

(21) Appl. No.: 12/583,512

(22) Filed: Aug. 20, 2009

(65) Prior Publication Data

US 2010/0095971 A1 Apr. 22, 2010

Related U.S. Application Data

(60) Provisional application No. 61/196,956, filed on Oct. 21, 2008.

(51) Int. Cl.
*A61F 11/00* (2006.01)
*H04R 25/02* (2006.01)
(52) U.S. Cl. .................. 128/865; 181/130; 381/312
(58) Field of Classification Search .............. 128/865, 128/864, 857, 846; 181/126, 128, 130, 135; 381/312, 322, 328; 604/317, 358
See application file for complete search history.

(56) References Cited

U.S. PATENT DOCUMENTS

| 4,408,605 | A | | 10/1983 | Doerr et al. | |
|---|---|---|---|---|---|
| 4,434,794 | A | | 3/1984 | Leight | |
| 4,579,112 | A | | 4/1986 | Scott | |
| 5,452,731 | A | * | 9/1995 | Dickman | 128/864 |
| 5,954,682 | A | * | 9/1999 | Petrus | 604/1 |
| 6,938,621 | B1 | | 9/2005 | Greenhaw et al. | |
| 7,697,706 | B2 | * | 4/2010 | Doty | 381/328 |
| 2007/0148409 | A1 | * | 6/2007 | Rios et al. | 428/167 |
| 2008/0187159 | A1 | * | 8/2008 | Blanchard | 381/328 |

* cited by examiner

*Primary Examiner* — Patricia Bianco
*Assistant Examiner* — Tarla Patel

(57) ABSTRACT

By providing an ear plug product incorporating water absorbing capabilities, a highly effective and easily employed ear plug product is realized which is capable of being used for removing water contained in the ear canal of an individual. In one preferred embodiment, the ear plug product of the present invention incorporates water absorbing material integrally formed in the ear plug which immediately draws the water from the ear canal into the ear plug product for being retained in the ear plug. In an alternate preferred embodiment, the ear plug product incorporates at least one elongated, longitudinally extending channel or passageway formed along substantially the entire length of the ear plug product. By incorporating the elongated, longitudinally extending passageway or channel in the ear plug product, the desired water absorption is achieved.

13 Claims, 3 Drawing Sheets

WATER ABSORBING EAR PLUGS

RELATED DATA

This application claims the benefit of U.S. Provisional Patent Application Ser. No. 61/196,956, filed Oct. 21, 2008 entitled Water Absorbing Ear Plugs.

TECHNICAL FIELD

This invention relates to ear plug products and, more particularly, to ear plug products constructed for ease of insertion in the ear canal and incorporating water absorbing compositions.

BACKGROUND ART

One problem which has continuously plagued individuals without a satisfactory solution or remedy being made available is the annoying and potential hazardous effects produced by having water trapped in the ear of an individual. Anyone who has suffered with this problem is well aware of the extreme difficulty in successfully removing water droplets from their ear canal. Furthermore, since a small amount of water can cause hearing to be less acute, affect an individual's balance, and cause potential health risks, the removal of the water from the ear is important to achieve.

Although various folk remedies and dangerous practices are often suggested as a cure, these various procedures and practices have proven to be incapable of satisfactorily removing water from an individual's ear as well as being potentially dangerous and causing harm to the eardrum or the ear canal. However, in spite of the continuing existence of this problem, as well as the numerous occasions in which individuals are exposed to having water enter the ear canal, such as when bathing, swimming, showering, and the like, a satisfactory resolution of this problem has not been achieved.

In particular, no prior art product has been developed or has become commercially available which is quickly and easily employed by any individual for safely removing water which has entered the ear canal. As a result, in spite of the existence of this problem for numerous decades, no product has been developed which is capable of successfully resolving these issues and the difficulties and complications being suffered by numerous individuals.

Therefore, it is a principal object of the present invention to provide an easily employed product which is able to be inserted quickly and conveniently into the ear of any individual for removing water contained in the ear canal.

Another object of the present invention is to provide an easily employed product having the characteristic features described above which is in the form of an ear plug constructed for quickly and conveniently absorbing any water contained in the ear canal of an individual.

Another object of the present invention is to provide an ear plug product having the characteristic features described above which is soft and compressible for being easily formed into a shape for insertion ease.

Another object of the present invention is to provide an ear plug product having the characteristic features described above which incorporates a water absorbing composition contained therein for providing the desired result.

Other and more specific objects will in part be obvious and will in part appear hereinafter.

SUMMARY OF THE INVENTION

By employing the present invention, all of the difficulties and drawbacks found in the prior art had been eliminated and a highly effective and easily employed ear plug product is realized which is capable of being used for removing water contained in the ear canal of an individual. In accordance with the present invention, an ear plug product is constructed from soft, compressible, pliable, and readily deformable material which is formulated for being easily held by a user and formed into a small and compact size for being easily inserted into the ear canal of the user. Once inserted into the ear canal of the user, the ear plug product returns to its substantially original size, substantially filling the ear canal.

In addition, in one preferred embodiment, the ear plug product of the present invention incorporates water absorbing material integrally formed therein which immediately draws the water from the ear canal into the ear plug product for being retained in the ear plug. In this way, all water contained in the ear canal of an individual is quickly and easily absorbed by the ear plug product of the present invention for retention in the ear plug and complete removal from the ear canal once the plug is removed.

In the first preferred embodiment, the ear plug product of the present invention is constructed from polyurethane foam material which is configured for being soft and readily compressible. In addition, in its preferred embodiment, the ear plug product is constructed in an elongated, generally cylindrical shape which gently tapers from one end to the other, resulting in an ear plug product having a larger diameter at one end and a smaller diameter at the opposed end. In addition, the smaller diameter end of the ear plug product is preferably rounded to provide a smooth, continuous, curved contoured shape.

In the preferred construction, the polyurethane foam material is formulated for being easily manipulated in the hands of the user in order to enable the ear plug product to be easily rolled and formed into a smaller diameter configuration. In this way, the ear plug product can be quickly and easily formed into a configuration which is easily inserted into the ear canal of the user.

In addition, the polyurethane foam material employed for the present invention is also constructed with an elastic memory which enables the ear plug product to automatically return to its substantially original configuration once compressive forces had been removed. As a result, once the ear plug product has been compressed and inserted into the ear canal of the user, the ear plug product automatically returns to its original size and shape, substantially filling the ear canal of the user.

In the preferred construction of this embodiment of the ear plug product of the present invention, a water absorbing polymer is integrated into the polyurethane foam material for automatically drawing any water in the ear canal of the user into the ear plug product, once the ear plug product has been inserted into the ear canal of the user. In this way, all of the water retained in the ear canal and causing pain, discomfort, and possible injury to the user is automatically removed from the ear canal and absorbed directly into the ear plug product. The preferable water absorbing polymer is 2,5 Furandione with 2-methyl-1-propene, also known as maleic anhydride. However, other similar compositions can be employed with equal efficacy.

In this way, water retained in the ear canal is directly, conveniently, and easily removed in its entirety by merely inserting the ear plug product of the present invention into the affected ear canal and allowing sufficient time for the water in the ear canal to be absorbed into the ear plug product. When sufficient time has elapsed, the ear plug product with the water retained therein is removed, resulting in complete relief to the user.

In a second preferred embodiment of the present invention, the ear plug product is constructed from soft, compressible, pliable, and readily deformable material as detailed above in regard to the first embodiment. In addition, the material employed in this alternate embodiment is also formulated for being easily held by a user and formed into a small and compact size for being easily inserted into the ear canal of the user. Furthermore, once inserted into the ear canal of the user, this alternate embodiment of the ear plug product returns to its substantially original size, substantially filling the ear canal.

In the second preferred embodiment, the ear plug product of the present invention is constructed in a unique manner by incorporating at least one elongated, longitudinally extending channel or passageway formed along substantially the entire length of the ear plug product. In the preferred construction, the elongated, longitudinally extending channel or passageway is formed along the central axis of the ear plug product and comprises a diameter ranging between about 0.05 and 3 mm. If desired, a plurality of substantially parallel, elongated channels may be employed.

It has been found that by incorporating the elongated, longitudinally extending passageway or channel in the ear plug product, the desired water absorption is achieved without requiring the use of water absorbing polymers in the polyurethane foam material. In this regard, it has been found that by merely inserting the ear plug product of the present invention into an ear canal in which water is present, the water contacts the terminating end of the ear plug product and is automatically transferred from the ear canal into the elongated channel due to capillary action.

Regardless of the diameter of the elongated passageway or channel which results from the insertion of the ear plug product into the ear canal, the abutting engagement of the terminating end of the ear plug product with the water in the ear canal enables capillary action to automatically draw the water from the ear canal into the elongated channel or passageway, enabling the water to be transferred along the entire length of the channel or passageway through to its opposed terminating end. In this way, all of the water retained in the ear canal is automatically removed.

By employing the second alternate preferred embodiment of the present invention, an ear plug product is achieved which is capable of removing any water retained in the ear canal. Furthermore, by employing this second preferred embodiment, the ear plug product may be formed of only polyurethane foam material, without requiring the incorporation of water absorbing polymers into the polyurethane foam. However, if desired, water absorbing polymers may be incorporated into the polyurethane foam of the ear plug product, along with the longitudinally extending, canal or passageway. In this way, a product is realized which provides further enhanced, multi-purpose operational constructions for assuring the complete removal of all water contained in the ear canal.

Although polyurethane foam material has been found to be readily available, easily employable and highly effective in providing all of the attributes desired for the ear plug product of the present invention, any other polymer foam materials, plastic materials, elastomeric materials, or thermoplastic materials having similar attributes can be employed with equal efficacy. Consequently, although polyurethane foam materials is preferred, any of these other materials can also be employed without departing from the scope of the present invention.

The invention accordingly comprises a product possessing the features, properties, and the relation of components which will be exemplified in the product hereinafter described, and the scope of the invention will be indicated in the claims.

THE DRAWINGS

For a fuller understanding of the nature and objects of the invention, reference should be had to the following detailed description taken in connection with the accompanying drawings, in which.

DETAILED DISCLOSURE

By referring to FIGS. 1-5, along with the following detailed discussion, the construction and operation of the two preferred embodiments of the water absorbing ear plug product of the present invention can best be understood. It is to be understood, however, that this detailed disclosure is provided for exemplary purposes only and is not intended as a limitation of the present invention. As a result, since the present invention can be implemented using alternate formulations and constructions, it is to be understood that these alternate embodiments are intended to be included in the scope of the present invention with the following detailed disclosure being provided merely for fully detailing the best mode of the present invention.

Figure 1:
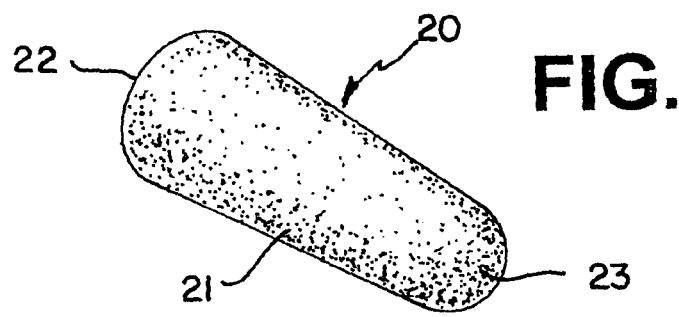
FIG. 1 is a perspective view of a first preferred embodiment of the ear plug product of the present invention.
Figure 2:
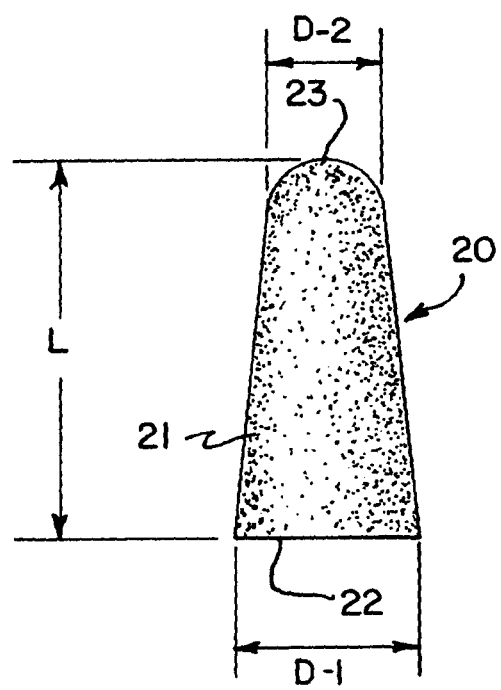
FIG. 2 is a side elevation view of the ear plug product of FIG. 1.

In FIGS. 1 and 2, the first preferred embodiment of ear plug product 20 is fully depicted in its preferred configuration. As shown, ear plug product 20 preferably comprises a generally cylindrically shaped member 21 which comprises a tapered cylindrical shape. In this regard, cylindrically shaped member 21 comprises a larger diameter, rear terminating end 22 and opposed, smaller diameter front terminating end 23. Furthermore, front terminating end 23 is also preferably formed with a convex, arcuately curved shape which provides a smooth, continuous surface for enabling front terminating end 23 to be easily inserted into the ear canal of the user.

As depicted, rear terminating end 22 preferably comprises a substantially flat surface for being easily held up by the user. However, as is evident from this disclosure, any alternate configuration, size, or shape can be employed without departing from the scope of this invention.

In its preferred construction, ear plug product 20 is constructed from polyurethane foam material in order to enable ear plug product 20 to be easily employed by the user. In this regard, as discussed above, ear plug product 20 is constructed for being easily held in the hand of the user for being rolled, squeezed, and/or compressed in its entirety, in order to form cylindrically shaped member 21 into a smaller diameter configuration. Once ear plug product 20 has been compressed into its smaller diameter configuration, ear plug product 20 is quickly and easily inserted into the ear canal of the user.

In order to enable ear plug product 20 of the present invention to be easily employed in the desired manner by the user, polyurethane foam is molded into precisely desired shape depicted in FIGS. 1 and 2 and discussed above. In this regard, however, as also discussed above, alternate shapes sizes and configurations can be employed with equal efficacy.

In the preferred construction, the molded polyurethane foam employed for ear plug product 20 comprises physical properties which are specifically constructed to enable ear plug product 20 of the present invention to function in the desired manner. Although a wide variety of physical properties are taken into consideration for achieving an optimal product, several specific physical properties are of particular interest and importance.

In this regard, the density of the molded polyurethane foam material represents an important factor, and, in the preferred embodiment, the molded polyurethane foam material is configured with a density of between about 5 and 10 pounds per cubic foot, with 7.8 pounds per cubic foot being preferred. In addition, the polyurethane foam material also comprises a compression force deflection (CFD) of between about 0.5 and 1.0 psi at 50%. Preferably, a CFD of 0.70 psi at 50% is preferred.

In this regard, the compression force deflection (CFD) is the determination or measurement of the resistance to compression of the flexible polyurethane foam sample when the entire surface area of the sample is compressed. The test method employed for determining the CFD is described in ASTM D3574.

Another important factor in providing a polyurethane foam material which achieves all of the desired physical properties is the ball rebound of the material which is employed to measure the surface resiliency of the flexible polyurethane foam. In order to determine ball rebound, a steel ball of known mass is dropped from a predetermined height onto a sample of the flexible polyurethane foam material. The rebound height attained by the steel ball, expressed as a percent-age of the original drop height, is the ball rebound resiliency value. This test method is fully detailed in ASTM D3574. In accordance with the present invention, the ball rebound of the prefer polyurethane foam material ranges between about 3% and 8%, with 4.7% being preferred.

Finally, the preferred durometer or shore hardness of the polyurethane foam material employed in the present invention preferably ranges between about 50 and 70, with 62 being preferred. As is well known, the durometer of the polyurethane foam material is a measurement of the hardness of the material.

By constructing ear plug product 20 from a polyurethane foam material having the attributes detailed above, an ear plug product is achieved which is capable of providing the flexibility, ease of use, compressibility, deformability, and recovery required for achieving the goals of the present invention. In this way, an easily manufactured and employed product is realized.

In FIG. 2, ear plug product 20 is depicted along with the overall dimensions for the ear plug product 20. In this regard, the length of the ear plug product 20 is designated as "L", the diameter of the rear terminating end 22 is designated as "D-1", and the diameter of the front terminating end 23 is designated as "D-2". In this regard, although a wide range of the dimensions can be employed for forming ear plug product 20 in accordance with the present invention, the preferred length or "L" of ear plug product 20 ranges between about 0.8 inches and 1.5 inches, with 1.03 inches being preferred. In addition, diameter "D-1" ranges between about 0.35 inches and 0.6 inches, with 0.47 inches being preferred, while diameter "D-2" ranges between about 0.26 inches and 0.42 inches, with 0.36 inches being preferred.

Although the specific detailed dimensions are provided, these dimensions are provided as the best mode for achieving the present invention. However, it should be understood, that variations and alterations can be made in the specific dimensions without departing from the scope of this invention.

Furthermore, although a sloping, tapered or truncated, cylindrical shape is preferred, any alternate shape can be employed with equal efficacy. In this regard, the principal requirement is a construction which is dimensioned for enabling the ear plug product 20 to be inserted into the ear canal of the user in a manner which will enable all of the goals and objectives of the present invention to be achieved. As long as this requirement is met, the particular shape, configuration, or other visual appearance of the ear plug product 20 is not significant.

Figure 3:
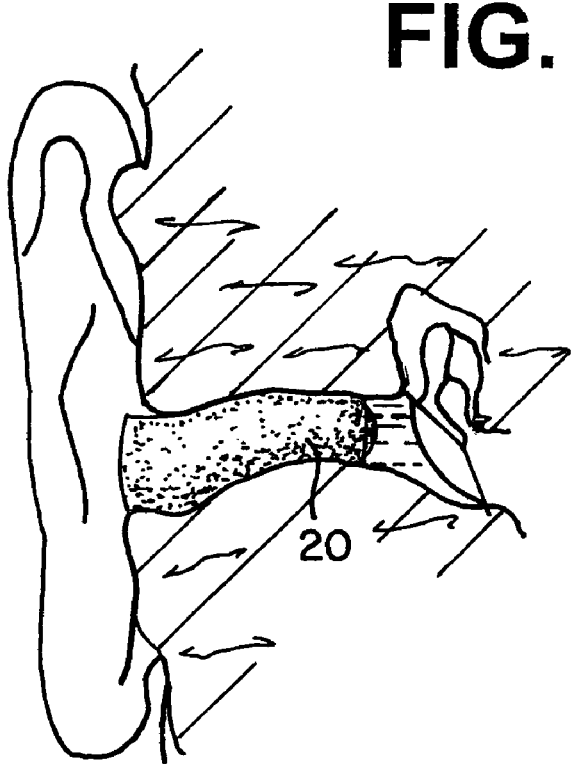
FIG. 3 is a perspective view of the ear plug product of the present invention in an individual's ear canal.

For exemplary purposes, FIG. 3 depicts ear plug product 20 positioned in an ear canal of a user. In this regard, as depicted, ear plug product 20 longitudinally extends into the ear canal of the user, with front terminating end 23 of ear plug product 20 positioned inwardly in the ear canal, while rear terminating end 22 is positioned directly adjacent the terminating entry opening to the ear canal. By positioning ear plug product 20 in this way, the tapered, cylindrical shape incorporated into ear plug product 20 enables the insertion of ear plug product 20 into the ear canal in a quickly and easily achieved manner. Furthermore, by forming ear plug product 20 with the desired overall length, ear plug product 20 extends into the ear canal a sufficient distance to reach any water retained in the ear canal for effectively absorbing and completely removing the undesirable water retained therein.

A principal requirement of the two embodiments of the present invention is the incorporation of a water absorbing component in the polyurethane foam material of ear plug product 20. In accordance with the present invention, it has been found that 2,5-Furandione polymer with 2-methyl-1-propene is employed as the water absorbing component. This water absorbing component is also known as maleic anhydride and dihydro-2,5-furandione.

In order to achieve the goals of the present invention, it has been found that between about 0.03 and 0.5 percent by weight based upon the weight of the entire composition of the water absorbing component is incorporated into the polyurethane foam material. In this regard, the preferred quantity of the water absorbing material has been found to be 0.1 percent by weight based by the weight of the entire composition.

By constructing ear plug product 20 in the manner detailed above, a highly effective water absorbing ear plug product 20 is achieved. Using the teaching of the present invention, it has been found that ear plug product 20 can be quickly and easily formed into a small diameter product which is quickly and easily inserted into the ear canal of the user, as shown in FIG. 3. Once ear plug product 20 has been placed in the desired position, ear plug product 20 automatically returns to its original dimensions, substantially filling the ear canal.

Once in position, any water contained in the ear canal is absorbed into ear plug product 20, completely removing the water from the ear canal. After a sufficient period of time has elapsed, typically 2 to 15 minutes, ear plug product 20 can be removed from the ear canal along with all of the water previously contained therein. In this way, the previous inabilities found in prior art systems are completely overcome and a fast, safe, effective, and easily employed water absorbing product is realized.

In addition to the water absorbing compositions detailed above, it has also been found that other compositions can be employed for providing water absorbing properties. In this regard, one a more compositions selected from the group consisting of citric acid, glycerin, propylene glycol, sodium acid pyrophosphate, sodium citrate, and triethanolamine can also be employed for providing similar water absorbing qualities.

It has also been discovered that ear plug product 20 of the present invention may also be manufactured with alternate compositions, formulations, or materials incorporated therein for assisting in the safe removal of wax from the ear canals. In this regard, it has been found that by incorporating one or more compositions selected from the group consisting of ethylene glycol, citric acid, glycerin, propylene glycol, sodium acid pyrophosphate, sodium citrate, and triethanolamine can be employed for softening earwax in the ear canal and enabling its safe and efficient removal. In this way, another difficult problem which prior art systems have been incapable of eliminating is efficiently and effectively resolved.

Figure 4:
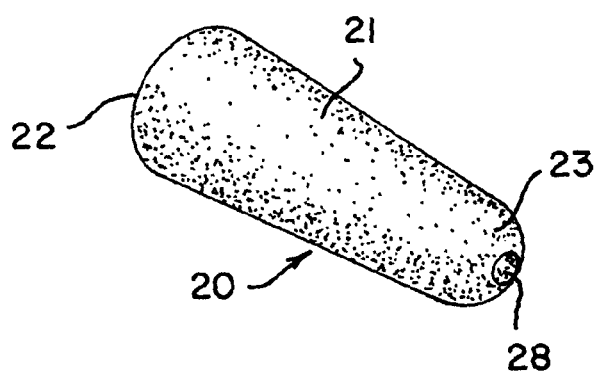
FIG. 4 is a perspective view of a second preferred embodiment of the ear plug product of the present invention.
Figure 5:
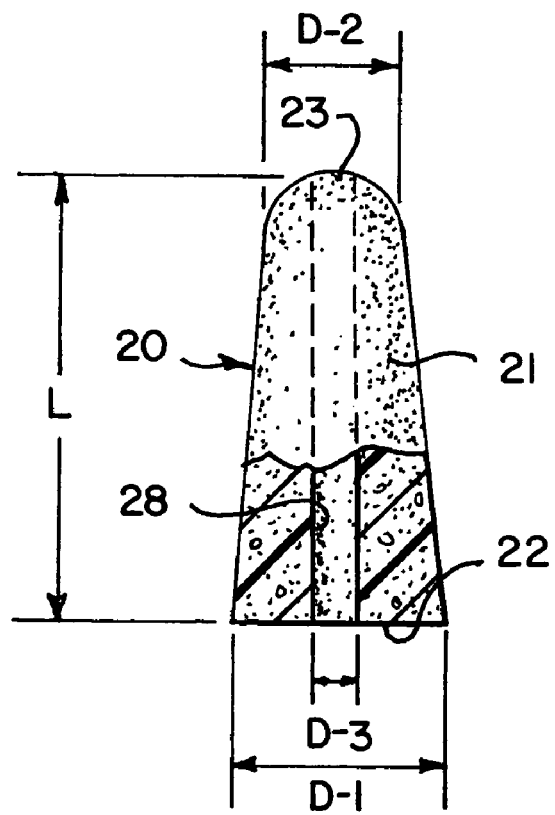
FIG. 5 is a cross-sectional side elevation view of the ear plug product of FIG. 4.

By referring to FIGS. 4 and 5, along with the following detailed discussion, the construction of the second preferred embodiment of the ear plug product 20 can best be understood. As shown, this embodiment of ear plug product 20 also comprises a generally cylindrically shaped member 21 having larger diameter rear terminating end 22 and opposed, smaller diameter front terminating end 23. Furthermore, this embodiment also comprises front terminating end 23 preferably formed with a convex, arcuately curve shape which provides a smooth, continuous surface for enabling front terminating end 23 to be easily inserted into the ear canal of the user.

In addition, rear terminating end 22 preferably comprises a substantially flat surface for being easily held by the user for insertion in the ear canal of the user. However, as is evident from this disclosure, ear plug product 20 may be constructed in any alternate configuration, size, or shape without departing from the scope of this invention.

In FIG. 5, the overall dimensions of this embodiment of ear plug product 20 are fully depicted. In this regard, ear plug product 20 comprises an overall length designated as "L", with rear terminating end 22 comprising a diameter designated as "D-1", and front terminating end 23 comprising a diameter designated as "D-2".

In this embodiment of the present invention, ear plug product 20 incorporates longitudinally extending passageway or through hole 28 extending from rear terminating end 22 to front terminating end 23. As depicted, passage-way/hole 28 comprises a diameter designated as "D-3".

It has been found that by incorporating longitudinally extending, continuous, elongated passageway/hole 28 in ear plug product 20, any water which has been retained in the ear canal of an individual is automatically removed from the ear canal whenever ear plug product 20 is inserted into the ear canal. In this regard, it is believed that capillary action or hydrostatic pressure causes the water retained in the ear canal to be drawn through elongated passageway/hole 28, completely removing all of the water contained in the ear canal with ease and simplicity.

If desired, water absorbing components may be incorporated into the composition of the ear plug product 20 in combination with elongated passage-way/hole 28. Although the incorporation of the water absorbing components is not required, the additional incorporation of the water absorbing components into this embodiment of ear plug product 20 further enhances and improves the water absorbing capabilities of the resulting product.

In the preferred construction of this embodiment of the present invention, it has been found that diameter "D-3" of elongated passageway/hole 28 preferably ranges between about 0.04 inches and 0.1 inches, with 0.08 inches being preferred. In addition, it has also been found that overall length "L" of the ear plug product 20 comprises a greater length than employed with the first preferred embodiment. In this regard, length "L" of this embodiment preferably ranges between about 0.8 inches and 1.75 inches, with 1.15 inches being preferred.

The remaining dimensions of this second preferred embodiment of ear plug product 20 are substantially identical to the dimensions defined above for the first preferred embodiment of ear plug product 20. In this regard, diameter "D-1" of rear terminating end 22 ranges between about 0.35 inches and 0.6 inches, with 0.47 inches being preferred. Finally, diameter "D-2" of front terminating end 23 ranges between about 0.26 inches and 0.42 inches, with 0.36 inches being preferred.

In the preferred construction of this second preferred embodiment, ear plug product 20 is formed from polyurethane foam material as fully detailed above in regard to the first preferred embodiment. As a result of this construction, this embodiment of ear plug product 20 is also easily held in the hand of the user for being rolled, squeezed, and/or compressed in its entirety, in order to form cylindrically shaped member 21 into a small diameter configuration. Once ear plug product 20 has been compressed into its smaller diameter configuration, ear plug product 20 is quickly and easily inserted into the ear canal of the user.

Preferably, the polyurethane foam material is molded into the desired shape as depicted in FIGS. 4 and 5, incorporating the dimensions detailed above. However, as also discussed above, alternate sizes, shapes, and configurations can be employed with equal efficacy.

The molded polyurethane foam material employed for constructing this embodiment of ear plug product 20 is constructed in a manner substantially identical to the construction detailed above, thereby possessing the properties detailed above which specifically enable ear plug product 20 to function in the desired manner. Furthermore, this embodiment of the present invention is constructed to possess the specific physical properties identified above in regard to the first preferred embodiment with each of these properties being constructed to have identical values defined above.

In this regard, this second preferred embodiment of the ear plug product is constructed with the polyurethane foam material thereof possessing a density, compressive force deflection, ball rebound, and durometer, the values of which are substantially equivalent to the values of these properties as defined above. As a result, all of the attributes detailed above in regard to the first preferred embodiment of the present invention apply with equal efficacy to this second preferred embodiment.

Furthermore, although the water absorbing materials are not required, if such materials are included in the embodiment, the same materials detailed are preferably employed. In this way, additional water absorption is provided.

Figure 6:
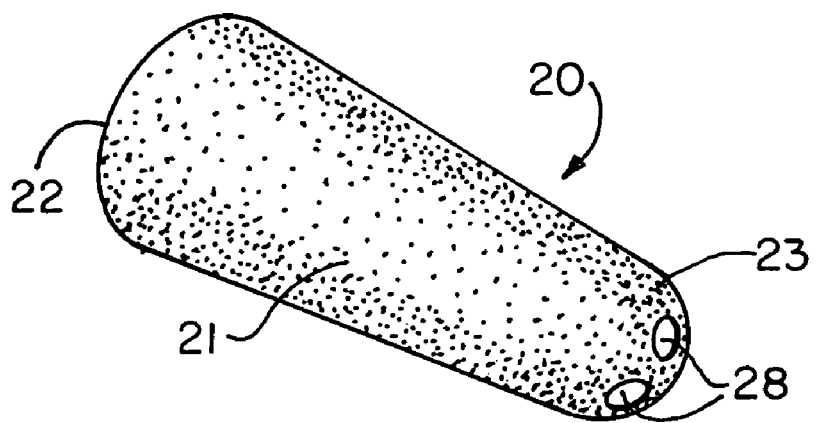
FIG. 6 is a perspective view of a third preferred embodiment of the ear plug product of the present invention.
Figure 7:
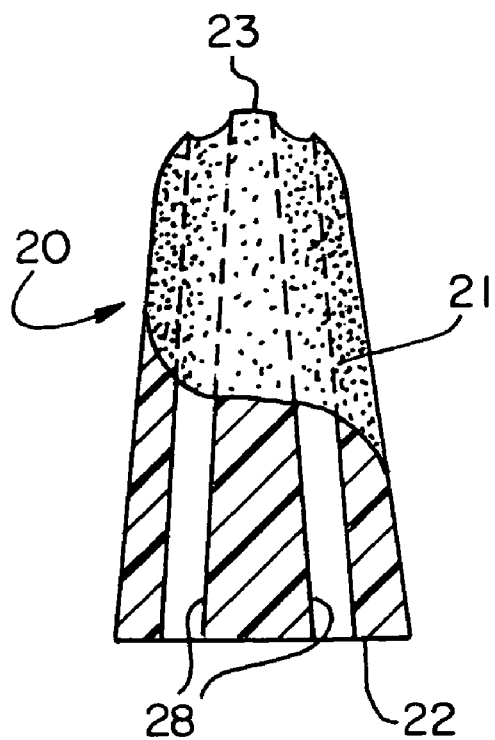
FIG. 7 is a cross-sectional side elevation view of the ear plug product of the ear plug product of FIG. 6.

By referring to FIGS. 6 and 7, along with the following detailed discussion, the construction of the third exemplary embodiment of the ear plug product 20 can best be understood. As shown, the third exemplary embodiment of ear plug product 20 comprises a generally cylindrically shaped member 21 having larger diameter rear terminating end 22 and opposed, smaller diameter front terminating end 23. Furthermore, the third exemplary embodiment also comprises front terminating end 23 preferably formed with a convex, arcuately curve shape which provides a smooth, continuous surface for enabling front terminating end 23 to be easily inserted into the ear canal of the user.

In addition, rear terminating end 22 preferably comprises a substantially flat surface for being easily held by the user for insertion in the ear canal of the user. However, as is evident from this disclosure, ear plug product 20 may be constructed in any alternate configuration, size, or shape without departing from the scope of this invention.

As shown in FIGS. 6 and 7, the ear plug product 20 incorporates a plurality of longitudinally extending passageways or through holes 28 extending from rear terminating end 22 to front terminating end 23, and formed in juxtaposed, spaced, parallel relationship to each other. It has been found that by incorporating one or more longitudinally extending, continuous, elongated passageways/holes 28 in the ear plug product 20, any water which has been retained in the ear canal of an individual is automatically removed from the ear canal whenever ear plug product 20 is inserted into the ear canal. In this regard, it is believed that capillary action or hydrostatic pressure causes the water retained in the ear canal to be drawn through the one or more elongated passageways/holes 28, completely removing all of the water contained in the ear canal with ease and simplicity.

If desired, water absorbing components may be incorporated into the composition of the ear plug product 20 in combination with the plurality of elongated passageways/holes 28. Although the incorporation of the water absorbing components is not required, the additional incorporation of the water absorbing components into this embodiment of ear plug product 20 further enhances and improves the water absorbing capabilities of the resulting product.

In an exemplary construction of the third exemplary embodiment, ear plug product 20 is formed from polyurethane foam material as fully detailed above in regard to the first and second preferred embodiments. As a result of this construction, the third exemplary embodiment of the ear plug product 20 is also easily held in the hand of the user for being rolled, squeezed, and/or compressed in its entirety, in order to form cylindrically shaped member 21 into a small diameter configuration. Once ear plug product 20 has been compressed into its smaller diameter configuration, ear plug product 20 is quickly and easily inserted into the ear canal of the user.

Preferably, the polyurethane foam material is molded into the desired shape as depicted in FIGS. 6 and 7. However, as also discussed above, alternate sizes, shapes, and configurations can be employed with equal efficacy.

The molded polyurethane foam material employed for constructing this embodiment of ear plug product 20 is constructed in a manner substantially identical to the construction detailed above, thereby possessing the properties detailed above which specifically enable ear plug product 20 to function in the desired manner. Furthermore, this embodiment of the present invention is constructed to possess the specific physical properties identified above in regard to the first and second preferred embodiments with each of these properties being constructed to have identical values defined above.

In this regard, this third exemplary embodiment of the ear plug product is constructed with the polyurethane foam material thereof possessing a density, compressive force deflection, ball rebound, and durometer, the values of which are substantially equivalent to the values of these properties as defined above. As a result, all of the attributes detailed above in regard to the first and second preferred embodiments of the present invention apply with equal efficacy to the third exemplary embodiment.

Furthermore, although the water absorbing materials are not required, if such materials are included in the third exemplary embodiment, the same materials detailed above with respect to the first and second preferred embodiments may be employed. In this way, additional water absorption is provided.

It will thus be seen that the objects set forth above, among those made apparent from the preceding description, are efficiently obtained and that, since certain changes may be made in the above products without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall their between.

Having described our invention, what we claim as new and desire to secure by Letters Patent is:

1. An ear plug comprising:
   an elongated, generally cylindrically shaped body dimensioned for ease of insertion and retention in an ear canal; and
   2,5-furandione polymer with 2-methyl-1-propene incorporated in the elongated, generally cylindrically shaped body for absorbing water retained in the ear canal and retaining the absorbed water in the elongated, generally cylindrically shaped body for enabling removal of the absorbed water from the ear canal.

2. The earplug defined in claim 1, wherein said elongated, generally cylindrically shaped body is further defined as comprising an overall tapered cylindrical shape defined by a substantially flat, larger diameter distal end and a substantially rounded, smoothly curved, convexly shaped, smaller diameter proximal end.

3. The ear plug defined in claim 2, wherein said elongated, generally cylindrically shaped body incorporates at least one elongated, continuous, longitudinally extending channel formed therein, with said channel extending from the distal end to the proximal end.

4. The ear plug defined in claim 3, wherein said at least one elongated channel is positioned for contacting any water retained in the ear canal and automatically absorbing the water into the elongated channel due to capillary action and/or hydostatic static forces.

5. The ear plug defined in claim 4, wherein the diameter of the at least one elongated channel is further defined as ranging between about 0.05 millimeters and 3 millimeters.

6. The earplug defined in claim 3, wherein said ear plug body incorporates a plurality of channels formed therein in juxtaposed, spaced, parallel relationship to each other.

7. The ear plug defined in claim 1, wherein said ear plug is further defined as being formed from at least one foam plastic material selected from the group consisting of polyurethane foam material, polymeric foam materials, plastic materials, elastomeric materials, and thermoplastic materials.

8. The ear plug defined in claim 7, wherein said foam plastic material is further, defined as being constructed for enabling said ear plug to be easily manipulated by an individual for being formed into a smaller diameter configuration to enable ease of insertion of the ear plug into the ear canal of the user, with the foam plastic material having an elastic memory to enable the automatic return of the ear plug to its original configuration.

9. The ear plug defined in claim 1, wherein said ear plug is formed from molded polyurethane foam material and comprises a density ranging between about 5 pounds per cubic foot and 10 pounds per cubic foot.

10. The ear plug defined in claim 9, wherein said ear plug is further defined as comprising a compression force deflection ranging between about 0.5 pounds per square inch and 1.0 pounds per square inch.

11. The ear plug defined in claim 10, wherein said ear plug comprises a ball rebound resiliency value ranging between about 3% and 8%, while also comprising a durometer or shore hardness ranging between about 50 and 70.

12. The ear plug defined in claim 1, wherein said ear plug comprises at least one ear wax treatment composition formed therein for softening earwax in the ear canal and enabling the safe removal thereof.

13. The ear plug defined in claim 12, wherein said ear wax treatment composition comprises one or more selected from the group consisting of ethylene glycol, citric acid, glycerin, propylene glycol, sodium acid pyrophosphate, sodium citrate, and triethanolamine.

* * * * *